United States Patent
Zhang et al.

(10) Patent No.: US 11,802,137 B2
(45) Date of Patent: Oct. 31, 2023

(54) METHOD FOR PREPARING INTERMEDIATE BY REDUCED GLUTATHIONE-INDICATED AMINO ACID MAILLARD REACTION

(71) Applicants: Jiangnan University, Wuxi (CN); Anhui Qiangwang Flavouring Food Co., Ltd., Jieshou (CN)

(72) Inventors: Xiaoming Zhang, Wuxi (CN); Siyun Lu, Wuxi (CN); Heping Cui, Wuxi (CN); Junhe Yu, Wuxi (CN); Huan Zhan, Wuxi (CN); Yun Zhai, Wuxi (CN); Wei Tang, Wuxi (CN); Jingyang Yu, Wuxi (CN); Shuqin Xia, Wuxi (CN)

(73) Assignees: Jiangnan University, Wuxi (CN); Anhui Qiangwang Flavouring Food Co., Ltd., Jieshou (CN)

( * ) Notice: Subject to any disclaimer, the term of this patent is extended or adjusted under 35 U.S.C. 154(b) by 585 days.

(21) Appl. No.: 17/251,207

(22) PCT Filed: Jul. 8, 2020

(86) PCT No.: PCT/CN2020/100797
§ 371 (c)(1),
(2) Date: Dec. 11, 2020

(87) PCT Pub. No.: WO2021/017781
PCT Pub. Date: Feb. 4, 2021

(65) Prior Publication Data
US 2021/0198301 A1 Jul. 1, 2021

(30) Foreign Application Priority Data
Aug. 1, 2019 (CN) .......................... 201910708106.X

(51) Int. Cl.
| | |
|---|---|
| *C07H 1/06* | (2006.01) |
| *G01N 1/38* | (2006.01) |
| *G01N 1/40* | (2006.01) |
| *G01N 21/31* | (2006.01) |
| *G01N 21/78* | (2006.01) |
| *C07H 7/02* | (2006.01) |
| *C07H 7/06* | (2006.01) |

(52) U.S. Cl.
CPC .................. *C07H 1/06* (2013.01); *C07H 7/02* (2013.01); *C07H 7/06* (2013.01); *G01N 1/38* (2013.01); *G01N 1/4022* (2013.01); *G01N 21/31* (2013.01); *G01N 21/78* (2013.01); *G01N 2001/386* (2013.01); *G01N 2021/3125* (2013.01)

(58) Field of Classification Search
None
See application file for complete search history.

(56) References Cited

U.S. PATENT DOCUMENTS
2010/0151061 A1  6/2010  Morariu

FOREIGN PATENT DOCUMENTS
| CN | 110361473 A | 10/2019 |
|---|---|---|
| JP | 2008237124 A | 10/2008 |

OTHER PUBLICATIONS

Siyun Lu et al., Timely Addition of Glutathione for its Interaction with Deoxypentosone to Inhibit the Aqueous Maillard Reaction and Browning of Glycylglycine-Arabinose System, Journal of Agricultural and Food Chemistry, 2019, pp. 6585-6593, 67.
Wei Tang et al., N-(1-Deoxy-D-xylulos-1-yl)-glutathione: A Maillard Reaction Intermediate Predominating in Aqueous Glutathione-Xylose Systems by Simultaneous Dehydration-Reaction, Journal of Agricultural and Food Chemistry, 2019, pp. 8994-9001, 67.
Haining Xu et al., Correlating Enzymatic browning inhibition and antioxidant ability of Maillard reaction products derived from different amino acids, Journal of the Science of Food and Agriculture, pp. 4210-4218, 97(12).

*Primary Examiner* — Layla D Berry
(74) *Attorney, Agent, or Firm* — Bayramoglu Law Offices LLC

(57) ABSTRACT

A method for preparing an intermediate by a reduced glutathione-indicated amino acid Maillard reaction is provided. The method includes a two-stage reaction at an increased temperature. A reduced glutathione is added after different times of a low-temperature reaction, and a subsequent Maillard reaction is effectively inhibited on a basis wherein a substance is interacted with an intermediate degradation product to reduce a formation of colored substances. Comparing with a browning of Maillard products after a high-temperature stage, a reaction time with a best color inhibition effect is found to be the optimal preparation condition of the intermediate, and the intermediate is prepared in an aqueous medium at a low temperature under this optimal preparation condition. The method uses the water soluble reduced glutathione as a tracer to improve a tracing accuracy comparing to cysteine.

3 Claims, 5 Drawing Sheets

METHOD FOR PREPARING INTERMEDIATE BY REDUCED GLUTATHIONE-INDICATED AMINO ACID MAILLARD REACTION

CROSS REFERENCE TO THE RELATED APPLICATIONS

This application is the national stage entry of International Application No. PCT/CN2020/100797, filed on Jul. 8, 2020, which is based upon and claims priority to Chinese Patent Application No. 201910708106.X, filed on Aug. 1, 2019, the entire contents of which are incorporated herein by reference.

TECHNICAL FIELD

The present invention relates to the field of food chemistry and food additives, and particularly relates to a method for preparing an intermediate by a reduced glutathione-indicated amino acid Maillard reaction.

BACKGROUND

Consumers' expectations for food tend to be more hierarchical and diversified with the development of the society and the age. There is an increasing demand for natural innovative products that are pleasant to the senses instead of satiety. Nowadays, the food industry presents a healthy, diverse and convenient development trend, and a processed flavor controlled formation technology is an important innovation direction of a food flavor control technology. With this technology, suitable flavor precursors can be prefabricated into flavoring semi-finished products according to processed food or catering needs. The products have not yet formed a complete flavor, but can quickly obtain a fresh and expected ideal flavor in the subsequent heat processing process. A Maillard reaction, also known as non-enzymatic browning, is widely present in the process of food processing and storage, and directly affects the flavor, taste, color and nutritional value of food, so it is one of the important research hotspots in the essence and flavor industry. At present, the food field mainly uses the products of an advanced Maillard reaction, but final products of the reaction are extremely unstable in that flavor substances are easily lost during high-temperature processing, so the application range is limited. In the primary stage of a Maillard reaction, intermediates, Amadori rearrangement product (ARP) and Heyns rearrangement product (HRP), formed by a reaction of amino compounds and carbonyl compound are two important types of flavor precursors. These two types of intermediates have relatively stable physical and chemical properties at low temperatures, but retain high reactivity under heating conditions, and the subsequent Maillard reaction can be easily completed to produce volatile flavor substances. Therefore, the intermediates have a broader application prospect in the food cooking and processing process than products of the advanced Maillard reaction.

There have been certain researches on the preparation of intermediates (ARP and HRP), most of which are synthesized in organic solvents such as methanol. These methods are serious in pollution and high in cost, which are only suitable for theoretical research and cannot meet the needs of large-scale production. In today's society, the concept of sustainable development is advocated, which refers to the coordinated development of economy, society, resources and environmental protection. Therefore, in industrial production, the concept of green, low carbon, environmental protection and sustainable development must be conceived as the purpose to coordinate economic costs and production safety. With a high-temperature Maillard reaction in aqueous medium, the cost can be reduced, but at a high temperature, amino acids and reducing sugars will rapidly undergo a series of cascade reactions, and the reaction process cannot be controlled, making it difficult to prepare intermediates. Using a cysteine tracer method to prepare Maillard reaction intermediates in aqueous medium is a new method proposed in recent years, which solves the above problems to a certain extent. However, cysteine has poor water solubility, leading to deviations in results due to incomplete dissolution, and the mechanism of cysteine as a tracer is unclear. Therefore, it is urgent to find a more suitable new tracer and researching a low-temperature aqueous medium controlled preparation theory and technical system of ARP and HRP to overcome the shortcomings of existing preparation technologies.

SUMMARY

In view of the defects in the prior art, the present invention provides a method for preparing an intermediate by a reduced glutathione-indicated amino acid Maillard reaction. The preparation method of the present invention is simple, safe to operate and low in cost.

The technical solution of the present invention is as follows:

The method for preparing an intermediate by a reduced glutathione-indicated amino acid Maillard reaction includes the following steps:

1) adding an amino acid and an aldose or ketose into water for a dissolution, and adjusting pH of a mixture to 6-8, wherein raw materials comprise by weight, 10 parts of amino acids, 10-40 parts of the aldose or the ketose and 200-1000 parts of the water;

(2) placing the mixture obtained in step (1) in water bath at a constant-temperature in 80-100° C. for a first-stage Maillard reaction, and taking out an equal volume of 5-8 samples in sequence from the mixture during this first-stage Maillard reaction at the 10th-180th minutes at an interval of 10-20 minutes and immediately placing the 5-8 samples in an ice bath for cooling to terminate a reaction to obtain first-stage Maillard reaction solutions;

(3) adding an equal amount of reduced glutathione into each sample of the 5-8 samples obtained in step (2) separately, re-adjusting the pH of the first-stage Maillard reaction solutions to 6-8 after uniform mixing, then transferring the first-stage Maillard reaction solutions into a temperature-resistant and pressure-resistant bottle for a second-stage high-temperature Maillard reaction at a same temperature in 110° C.-130° C. for 60-180 minutes and placing the second-stage Maillard reaction solutions in ice bath for cooling to terminate the reaction to obtain the second-stage Maillard reaction solutions;

(4) diluting the second-stage Maillard reaction solutions obtained in step (3) respectively, measuring absorbance value of each diluted second-stage Maillard reaction solution at a wavelength of 420 nm, drawing a curve diagram according to obtained absorbance values versus a corresponding reaction time of the diluted second-stage Maillard reaction in step (2), and determining the optimal reaction time under corresponding reaction conditions according to reaction time corresponding to lowest absorbance value;

(5) repeating the step (1): adding the amino acid and the aldose or the ketose into the water for the dissolution, and adjusting the pH of the mixed solution to 6-8, wherein amounts of the raw materials are based on the parts by weight used in step (1);

(6) placing the mixed solution obtained in step (5) in water bath at the temperature used in step (2), wherein a thermal treatment time is the optimal reaction time in step (4), immediately placing a product solution in ice bath for cooling to terminate the reaction to obtain a Maillard reaction intermediate solution;

(7) concentrating the Maillard reaction intermediate solution of first-stage Maillard reaction solution obtained in step (6) under a reduced pressure and a low temperature to remove 80%-90% water and then purifying the Maillard reaction intermediate solution by a cation exchange resin to obtain a pure Amadori rearrangement product (ARP) or Heyns rearrangement product (HRP), wherein The amino acid in step (1) is one or more of alanine, glycine, cysteine and proline. The aldose or ketose in step (1) is one or more of ribose, xylose and fructose.

The amounts of the raw materials in step (1) is: 10 parts of amino acids, 10-40 parts of the aldose or ketose and 200-1000 parts of water.

The cooling time in steps (2) and (3) is 10-30 minutes, and the reaction solutions are cooled to 10° C. or below to terminate the reaction.

an addition amount of the reduced glutathione in step (3) is 1%-2.5% w/v of a volume of the each sample of the 5-8 samples taken in step (2), wherein the 5-8 samples have the equal volume; and The reaction temperature in step (3) is 110-130° C.

In the solutions of second-stage Maillard reaction at increased temperature in step (4) are diluted 2-50 times with distilled water.

In step (7), the temperature is controlled to be 20-30° C. during concentration under reduced pressure and low temperature, and the vacuum degree is 0.025-0.05 MPa.

Beneficial Effects (1) By using amino acid Maillard reaction intermediates with stable physical and chemical properties to prepare prefabricated seasonings, the problem of easy loss of advanced Maillard reaction products during high-temperature processing is solved, the quality of processed food is improved in terms of overall flavor, the shortcoming of easy loss of flavors of existing advanced Maillard reaction essence products can be overcome, the transformation and upgrading of the food industry in China are promoted, and consumers are provided with delicious food while the sense of accomplishment and pleasure is enhanced. Due to complicated Maillard reaction paths and numerous products, there are still certain difficulties in preparation and detection of Maillard reaction intermediates, especially new intermediates. Usually, high performance liquid chromatography is used to detect the production amount of ARP or HRP, but this method requires preparation, purification and characterization of standard products first. Therefore, batch preparation of Maillard reaction intermediates encounters many difficulties to be solved urgently. An intermediate preparation method disclosed in the present invention has simple operation, feasibility and universality, and researches have confirmed that the preparation conditions determined by the method are completely consistent with the results of a high performance liquid chromatography assay.

(2) In existing disclosed technologies, there are only reports on cysteine used as a color inhibition and intermediate tracer of Maillard products, but the solubility of cysteine is low. Different addition concentrations of cysteine in a system have a significant impact on the color of final Maillard products. Therefore, once cysteine is not completely dissolved, concentration in the system is not uniform and the interaction with intermediates is not sufficient, errors in the browning value can be easily caused in the final stage, and the optimal preparation conditions are difficult to determine. In the present invention, reduced glutathione is used as a tracer, and the solubility of reduced glutathione in an aqueous solution is far higher than that of cysteine, so that the production time is greatly shortened, and industrial production is facilitated. In addition, optimal production conditions of intermediates can be more accurately traced, and the deficiency of using cysteine as a tracer is effectively overcome.

(3) For a tracer method which is a new method for preparing Maillard reaction intermediates, the mechanism of using cysteine as a tracer has not been clearly reported, and theoretically, different tracers also have different action mechanisms. In the present invention, on the basis that reduced glutathione has the effect of tracing Maillard reaction intermediates, the mechanism that the substance can be used as a tracer is further explored. The same two-stage Maillard reaction is adopted, it is found through researches that the oxidation product of reduced glutathione, namely oxidized glutathione, shows a gradual increase in the browning value during a high temperature stage with the increase of the first stage reaction time, indicating that the substance does not have the effect of tracing intermediates. The main difference in structure between reduced glutathione and oxidized glutathione is the presence or absence of free sulfhydryl, it can then be inferred that free sulfhydryl in reduced glutathione is the key factor for using reduced glutathione as a tracer. In addition, it is found through liquid chromatography and a liquid chromatography-mass spectrometry combined technology in the present invention that sulfhydryl of reduced glutathione can interact with an intermediate degradation product, subsequent Maillard cascade reactions can be effectively inhibited, the production of subsequent products such as glyoxal, pyruvaldehyde, furfural and other characteristic substances of a Maillard reaction is reduced, and Maillard reaction paths are changed, thereby reducing the formation of melanoidins to obtain light-colored flavor essences. Besides, the colors of final products obtained when intermediates are produced in large quantities and reduced glutathione is added are the lightest, which are consistent with the liquid chromatography verification results. It can be seen that reduced glutathione can be used as not only an intermediate tracer, but also a browning inhibitor. Based on existing reports, reduced glutathione and Maillard products thereof both have a mellow taste, and can give people a thick, rich, round and balanced taste experience, while cysteine does not have this effect. Therefore, if reduced glutathione is used as a flavor precursor by compounding with intermediates, not only can Maillard reaction characteristic flavors be formed through subsequent heat processing, but also a mellow taste can be provided to meet consumers' high requirement for taste richness, the use of salt, sugar and other seasonings is reduced, and the requirement for healthy diet proposed by modern people is met.

(4) Using reduced glutathione as a new tracer and determining the optimal preparation conditions of intermediates by measuring the browning degree of products of two-stage Maillard reaction in aqueous medium are the technological key and important breakthrough of controlled preparation of intermediates in aqueous medium, and the main drawbacks of an organic solvent preparation technology are overcome. In addition, the entire analysis and measurement work can be completed by only using a spectrophotometer, with a simple method, safe operation, a low cost and high feasibility. Large-scale production of ARP and HRP becomes possible by using this method to prepare Maillard reaction intermediates in a green, safe, directional and efficient manner in aqueous medium, and the practical application value is high.

DETAILED DESCRIPTION OF THE EMBODIMENTS

The following describes the present invention in detail with reference to the drawings and examples.

Example 1

(1) 17.8 kg of alanine and 60 kg of xylose are dissolved in 1000 kg of water, the pH of the mixed solution is adjusted to 8.0, a reaction is carried out at 80° C. under a water bath condition, and 180 L of a sample is taken at 40 minutes, 60 minutes, 80 minutes, 100 minutes and 120 minutes separately and placed in an ice bath for cooling to terminate the reaction.

(2) 1.8 kg of reduced glutathione is added into the five reaction solutions obtained above separately, the pH of the reaction solutions are re-adjusted to 8.0, and the reaction solutions are transferred into a temperature-resistant and pressure-resistant bottle, heated to 120° C. for a two-stage high-temperature Maillard reaction for 60 minutes and placed in an ice bath for cooling to terminate the reaction to obtain solutions of Maillard reaction at increased temperature.

Figure 1:
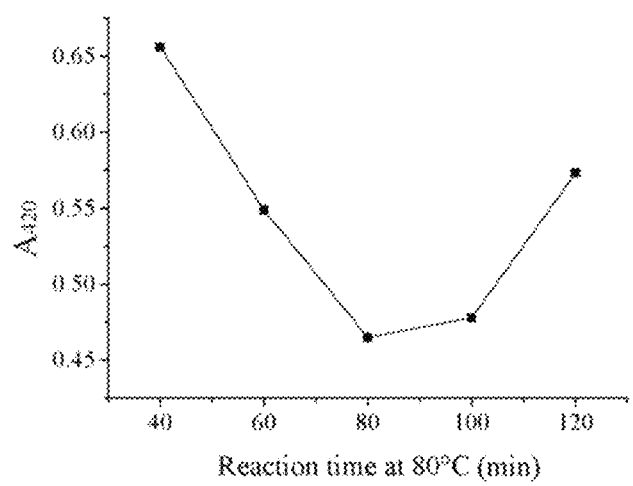
FIG. 1 is a curve diagram showing a relationship between the absorbance value of a solution of second-stage Maillard reaction at increased temperature after dilution and the Maillard reaction time of a first stage in Example 1 of the present invention.

(3) The solutions of Maillard reaction at increased temperature are diluted 5 times separately, the absorbance value at a wavelength of 420 nm is measured, a curve diagram is drawn according to the absorbance value and the corresponding low-temperature reaction time in step (1), and the results are as shown in FIG. 1. It can be seen from FIG. 1 that the reaction time corresponding to the low absorbance value of the solutions of Maillard reaction at increased temperature is 80 minutes, the best color inhibition effect is achieved, and thus it can be determined that the optimal reaction time in the first reaction stage at 80° C. is 80 minutes.

Figure 2:
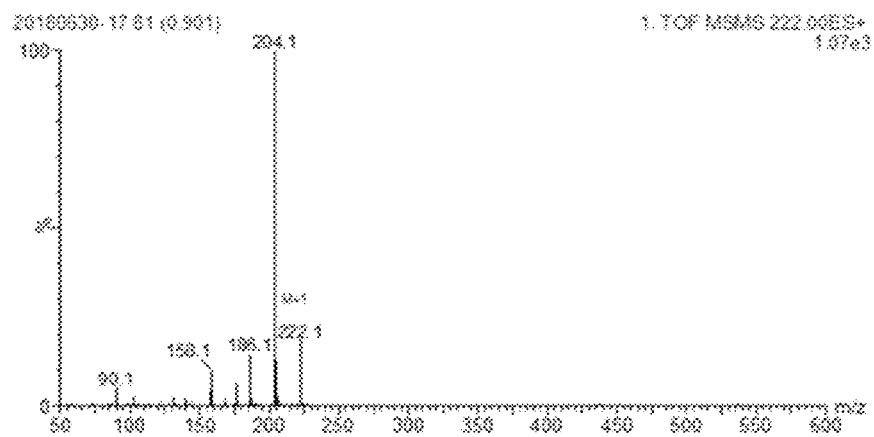
FIG. 2 is a mass spectrogram of ARP prepared in Example 1 of the present invention.
Figure 3A:
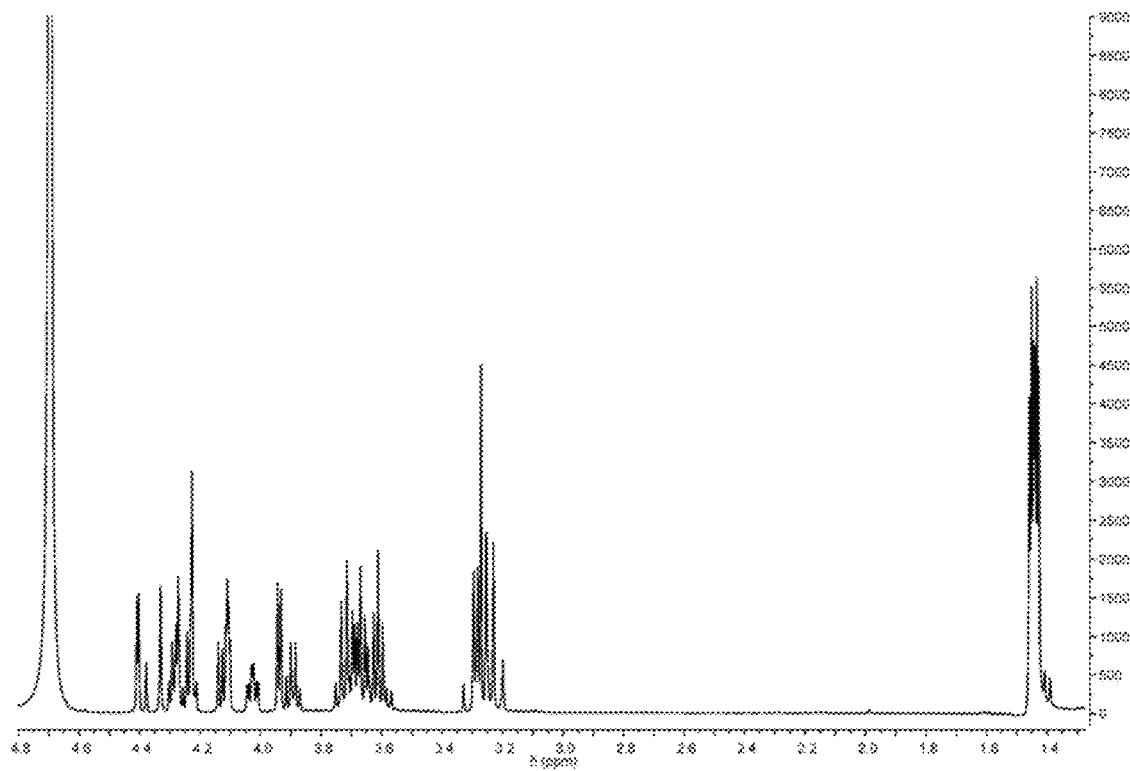
FIG. 3A shows a nuclear magnetic resonance hydrogen spectrogram of ARP prepared in Example 1.
Figure 3B:
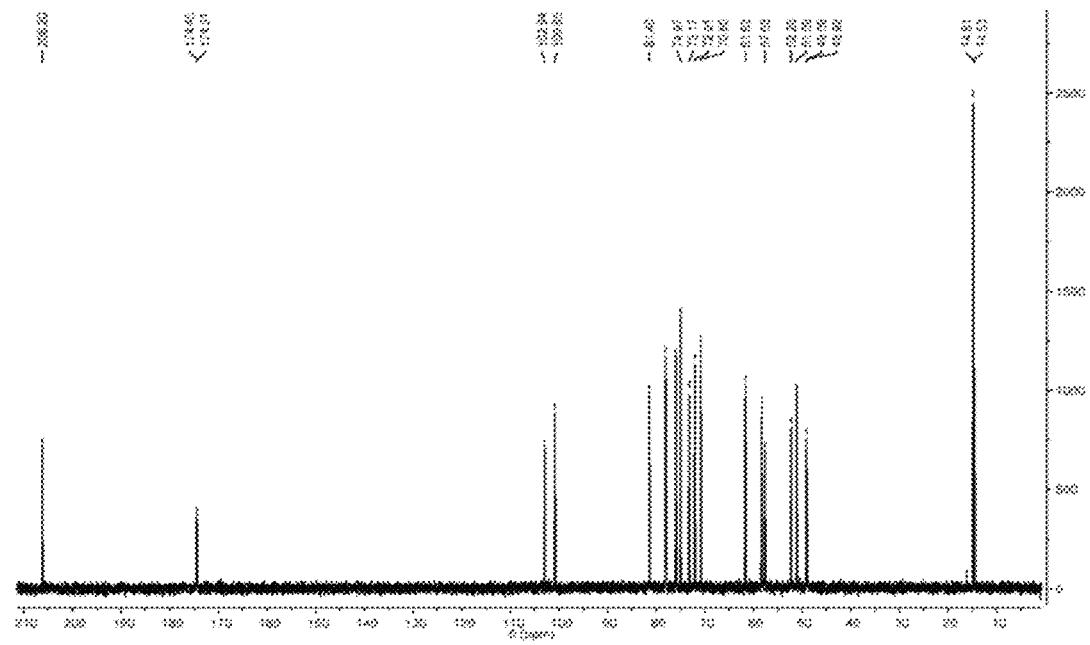
FIG. 3B shows a nuclear magnetic resonance carbon spectrogram of ARP prepared in Example 1.

An intermediate is prepared at the selected temperature and optimum time, further concentrated at a low temperature and then separated and purified by hydrogen type cation exchange resin to obtain a pure intermediate (ARP) of an alanine-xylose system, which is then freeze dried to obtain a solid sample. The obtained solid is dissolved in water and analyzed by using a mass spectrometry technology to obtain a mass spectrogram as shown in FIG. 2. The structural characterization of the solid is carried out by nuclear magnetic resonance to obtain a nuclear magnetic resonance spectrogram as shown in FIG. 3A and FIG. 3B.

Example 2

(1) 8 kg of cysteine and 19.8 kg of xylose are dissolved in 800 kg of water, the pH of the mixed solution is adjusted to 7.5, a reaction is carried out at 100° C. under a water bath condition, and 130 L of a sample is taken at 10 minutes, 20 minutes, 30 minutes, 40 minutes, 50 minutes and 60 minutes separately and placed in an ice bath for cooling to terminate the reaction.

(2) 1.3 kg of reduced glutathione is added into the six reaction solutions obtained above separately, the pH of the reaction solutions are re-adjusted to 7.5, and the reaction solutions are transferred into a temperature-resistant and pressure-resistant bottle, heated to 130° C. for a two-stage high-temperature Maillard reaction for 90 minutes and placed in an ice bath for cooling to terminate the reaction to obtain solutions of Maillard reaction at increased temperature.

Figure 4:
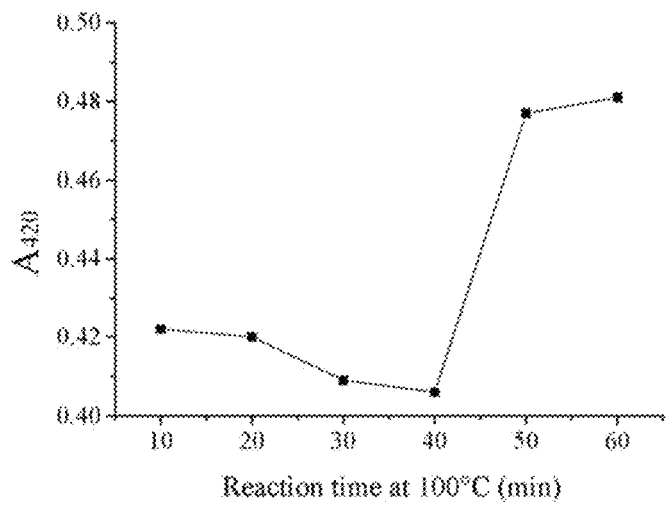
FIG. 4 is a curve diagram showing a relationship between the absorbance value of a solution of second-stage Maillard reaction at increased temperature after dilution and the Maillard reaction time of a first stage in Example 2 of the present invention.

(3) The solutions of Maillard reaction at increased temperature are diluted twice separately, the absorbance value at a wavelength of 420 nm is measured, a curve diagram is drawn according to the absorbance value and the corresponding low-temperature reaction time in step (1), and the results are as shown in FIG. 4. It can be seen from FIG. 4 that the reaction time corresponding to the low absorbance value of the solutions of Maillard reaction at increased temperature is 40 minutes, the best color inhibition effect is achieved, and thus it can be determined that the optimal reaction time in the first reaction stage at 100° C. is 40 minutes.

Figure 5A:
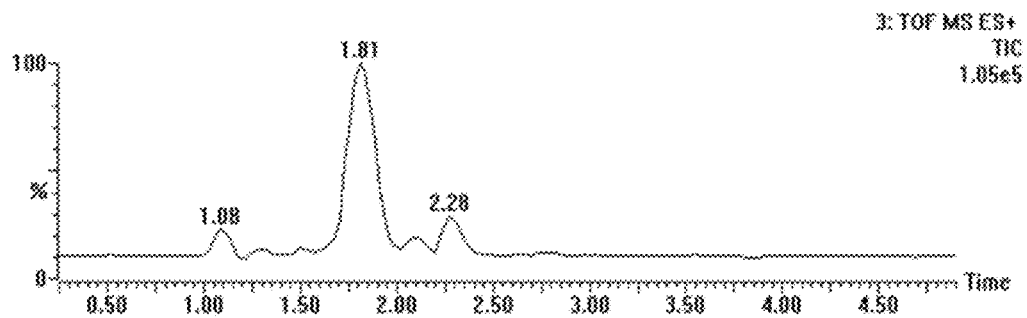
FIG. 5A is a total ion current chromatogram showing liquid chromatography-mass spectrometry characterization results of ARP prepared in Example 2 of the present invention.
Figure 5B:
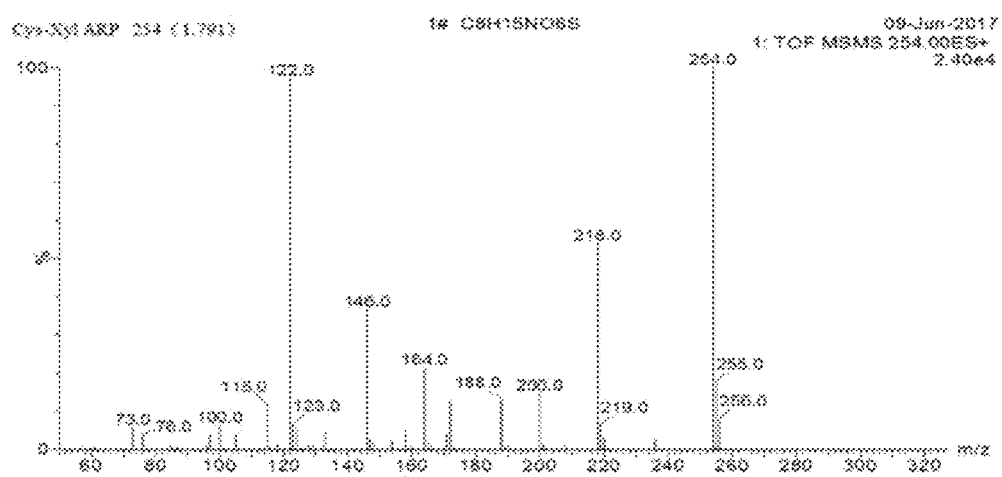
FIG. 5B is a mass spectrogram showing liquid chromatography-mass spectrometry characterization results of ARP prepared in Example 2 of the present invention.

An intermediate is prepared at the selected temperature and optimum time, further concentrated at a low temperature and then separated and purified by hydrogen type cation exchange resin to obtain a pure intermediate (ARP) of a cysteine-xylose system, which is then freeze dried to obtain a solid sample. The obtained solid is dissolved in water and analyzed by using a high performance liquid chromatography-mass spectrometry analysis technology to obtain a total ion current chromatogram and a mass spectrogram which are as shown in FIG. 5A and FIG. 5B.

Example 3

(1) 15 kg of glycine and 60 kg of ribose are dissolved in 1000 kg of water, the pH of the mixed solution is adjusted to 6.0, a reaction is carried out at 90° C. under a water bath condition, and 150 L of a sample is taken at 20 minutes, 40 minutes, 60 minutes, 80 minutes, 100 minutes and 120 minutes separately and placed in an ice bath for cooling to terminate the reaction.

(2) 3 kg of reduced glutathione is added into the six reaction solutions obtained above separately, the pH of the reaction solutions are re-adjusted to 6.0, and the reaction solutions are transferred into a temperature-resistant and pressure-resistant bottle, heated to 110° C. for a two-stage high-temperature Maillard reaction for 120 minutes and placed in an ice bath for cooling to terminate the reaction to obtain solutions of Maillard reaction at increased temperature.

Figure 6:
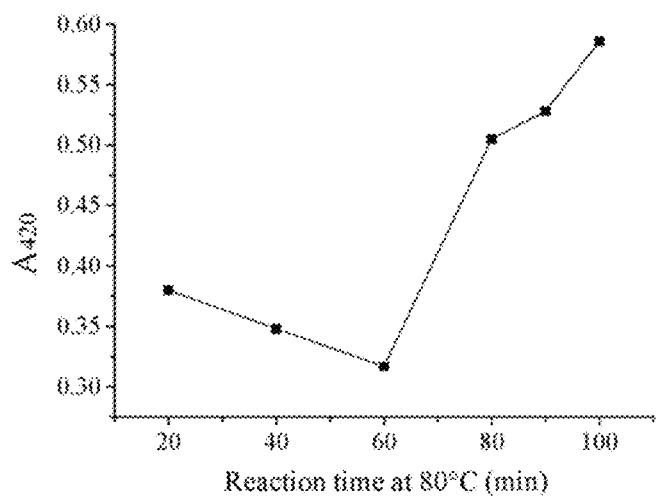
FIG. 6 is a curve diagram showing a relationship between the absorbance value of a solution of second-stage Maillard reaction at increased temperature after dilution and the Maillard reaction time of a first stage in Example 3 of the present invention.

(3) The solutions of Maillard reaction at increased temperature are diluted 50 times separately, the absorbance value at a wavelength of 420 nm is measured, a curve diagram is drawn according to the absorbance value and the corresponding low-temperature reaction time in step (1), and the results are as shown in FIG. 6. It can be seen from FIG. 6 that the reaction time corresponding to the low absorbance value of the solutions of Maillard reaction at increased temperature is 60 minutes, the best color inhibition effect is achieved, and thus it can be determined that the optimal reaction time in the first reaction stage at 90° C. is 60 minutes.

Figure 7A:
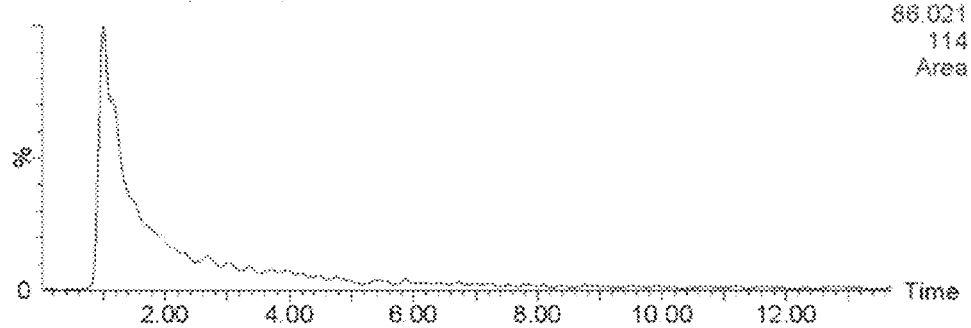
FIG. 7A is a total ion current chromatogram showing liquid chromatography-mass spectrometry characterization results of ARP prepared in Example 3 of the present invention.
Figure 7B:
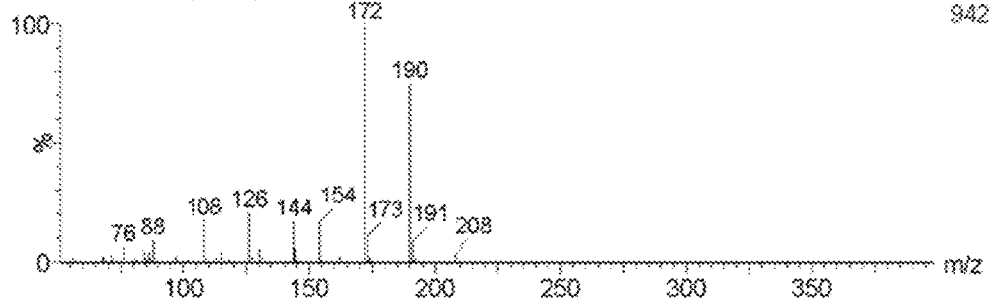
FIG. 7B is a mass spectrogram showing liquid chromatography-mass spectrometry characterization results of ARP prepared in Example 3 of the present invention.

An intermediate is prepared at the selected temperature and optimum time, further concentrated at a low temperature and then separated and purified by hydrogen type cation exchange resin to obtain a pure intermediate (ARP) of a glycine-ribose system, which is then freeze dried to obtain a solid sample. The obtained solid is dissolved in water and analyzed by using a high performance liquid chromatography-mass spectrometry analysis technology to obtain a total ion current chromatogram and a mass spectrogram which are as shown in FIG. 7A and FIG. 7B.

Example 4

(1) 20 kg of proline and 20 kg of fructose are dissolved in 400 kg of water, the pH of the mixed solution is adjusted to 7.0, a reaction is carried out at 100° C. under a water bath condition, and 80 L of a sample is taken at 100 minutes, 120 minutes, 140 minutes, 160 minutes and 180 minutes separately and placed in an ice bath for cooling to terminate the reaction.

(2) 20.0 kg of reduced glutathione is added into the five reaction solutions obtained above separately, the pH of the reaction solutions are re-adjusted to 7.0, and the reaction solutions are transferred into a temperature-resistant and pressure-resistant bottle, heated to 120° C. for a two-stage high-temperature Maillard reaction for 180 minutes and placed in an ice bath for cooling to terminate the reaction to obtain solutions of Maillard reaction at increased temperature.

Figure 8:
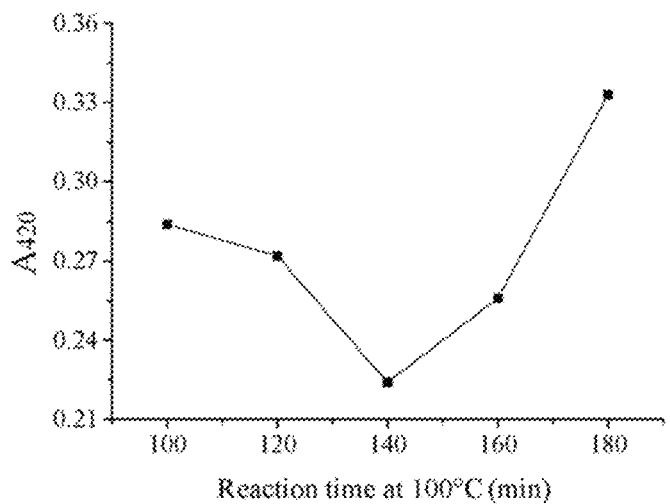
FIG. 8 is a curve diagram showing a relationship between the absorbance value of a solution of second-stage Maillard reaction at increased temperature after dilution and the Maillard reaction time of a first stage in Example 4 of the present invention.

(3) The solutions of Maillard reaction at increased temperature are diluted twice separately, the absorbance value at a wavelength of 420 nm is measured, a curve diagram is drawn according to the absorbance value and the corresponding low-temperature reaction time in step (1), and the results are as shown in FIG. 8. It can be seen from FIG. 8 that the reaction time corresponding to the low absorbance value of the solutions of Maillard reaction at increased temperature is 140 minutes, the best color inhibition effect is achieved, and thus it can be determined that the optimal reaction time in the first reaction stage at 100° C. is 140 minutes.

Figure 9:
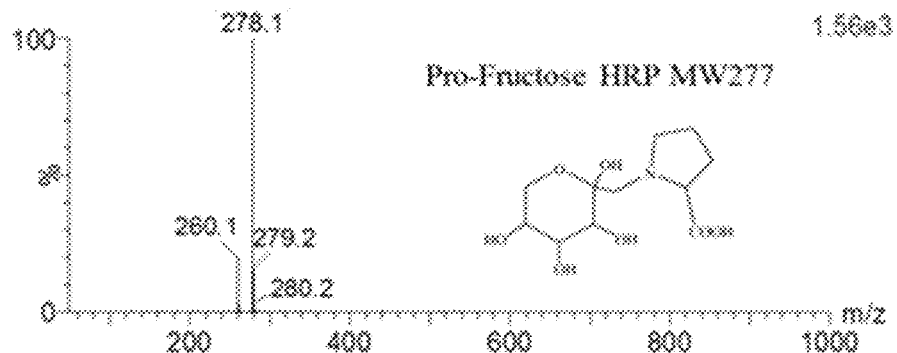
FIG. 9 is a mass spectrogram of HRP prepared in Example 4 of the present invention.

An intermediate is prepared at the selected temperature and optimum time, further concentrated at a low temperature and then separated and purified by hydrogen type cation exchange resin to obtain a pure intermediate (HRP) of a proline-fructose system, which is then freeze dried to obtain a solid sample. The obtained solid is dissolved in water and analyzed by using a mass spectrometry technology to obtain a mass spectrogram as shown in FIG. 9.

Comparative Example 1

Figure 10:
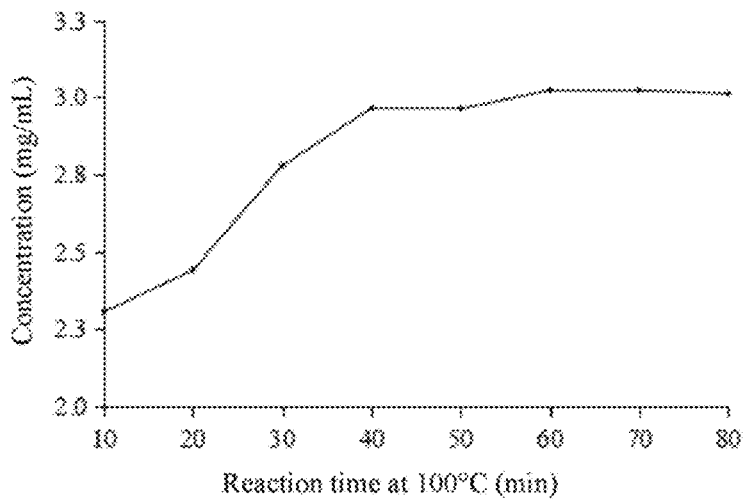
FIG. 10 is a curve diagram showing a relationship between the concentrations of ARP generated in a cysteine and xylose system and different low-temperature reaction times in Comparative Example 1.

8 kg of cysteine and 19.8 kg of xylose are dissolved in 800 kg of water, the pH of the mixed solution is adjusted to 7.5, a reaction is carried out at 100° C. under a water bath condition, a small amount of a sample is taken at different times and placed in an ice bath for cooling to terminate the reaction, the change rule of intermediate content at different reaction times is determined by high performance liquid chromatography, and the results are as shown in FIG. 10.

It can be seen from FIG. 10 that at the beginning of a low-temperature reaction stage, the cumulative amount of an intermediate in the system is gradually increased, and the content of an intermediate tends to be stable after 40 minutes, which corresponds to the lowest color point in FIG. 4. That is, in the cysteine-xylose system, the time for mass production of an intermediate is 40 minutes.

The experimental water in the above examples and comparative example is distilled water, aldose or ketose and amino acids are of food grade, chemical reagents used in high performance liquid chromatography-mass spectrometry analysis experiments are chromatographically pure, and the remaining chemical reagents are analytically pure. The detection conditions of high performance liquid chromatography are as follows: a chromatographic column CSHC18, a mobile phase containing acetonitrile and 0.1% formic acid water, a flow rate of 0.3 mL/min, gradient elution and a column temperature of 45° C. The conditions of mass spectrometry analysis are as follows: an ESI+ mode, a detector voltage of 1.8 kV, a capillary voltage of 3.5 kV, a cone voltage of 20 V and an extraction voltage of 7 V. The electron source temperature and the desolvation gas temperature are 100° C. and 400° C. respectively, the gas flow rate is 700 L/h, and the cone gas flow rate is 50 L/h. A sample is scanned in a mass ratio range of m/z20-1000, the scanning time is 1 second, and the scanning time delay is 0.1 second. A separated pure intermediate is dissolved in $D_2O$ and analyzed by a nuclear magnetic resonance instrument, and the test temperature is 298 K.

What is claimed is:

1. A method for preparing an intermediate by a reduced glutathione-indicated amino acid Maillard reaction, comprising the following steps:
   1) adding an amino acid and an aldose or ketose into water for a dissolution, and adjusting pH of a mixture to 6-8, wherein raw materials comprise by weight, 10 parts of amino acids, 10-40 parts of the aldose or the ketose and 200-1000 parts of the water;
   2) placing the mixture obtained in step 1) in water bath at a constant-temperature in 80-100° C. for a first-stage Maillard reaction, and taking out an equal volume of 5-8 samples in sequence from the mixture during this first-stage Maillard reaction at the 10th-180th minutes at an interval of 10-20 minutes and immediately placing the 5-8 samples in an ice bath for cooling to terminate a reaction to obtain first-stage Maillard reaction solutions;
   3) adding an equal amount of reduced glutathione into each sample of the 5-8 samples obtained in step 2) separately, re-adjusting the pH of the first-stage Maillard reaction solutions to 6-8 after uniform mixing, then transferring the first-stage Maillard reaction solutions into a temperature-resistant and pressure-resistant bottle for a second-stage high-temperature Maillard reaction at a same temperature in 110° C-130° C. for 60-180 minutes and placing the second-stage Maillard reaction solutions in ice bath for cooling to terminate the reaction to obtain the second-stage Maillard reaction solutions;
   4) diluting the second-stage Maillard reaction solutions obtained in step 3) respectively, measuring absorbance value of each diluted second-stage Maillard reaction solution at a wavelength of 420 nm, drawing a curve diagram according to obtained absorbance values versus a corresponding reaction time of the diluted second-stage Maillard reaction in step 2), and determining the optimal reaction time under corresponding reaction conditions according to reaction time corresponding to lowest absorbance value;
   5) repeating the operation of step 1): adding the amino acid and the aldose or the ketose into the water for the dissolution, and adjusting the pH of the mixed solution to 6-8, wherein amounts of the raw materials are based on the parts by weight used in step 1);
   6) placing the mixed solution obtained in step 5) in water bath at the temperature used in step 2), wherein a thermal treatment time is the optimal reaction time in step and, immediately placing a product solution in ice bath for cooling to terminate the reaction to obtain a Maillard reaction intermediate solution;
   7) concentrating the Maillard reaction intermediate solution of first-stage Maillard reaction solution obtained in step 6) under a reduced pressure and a low temperature to remove 80%-90% water and then purifying the Maillard reaction intermediate solution by a cation exchange resin to obtain a pure Amadori rearrangement product (ARP) or Heyns rearrangement product (HRP), wherein the amino acid in step 1) is one or more of alanine, glycine, cysteine and proline;
   the aldose or ketose in step 1) is one or more of ribose, xylose and fructose;
   an addition amount of the reduced glutathione in step 3) is 1%-2.5% w/v of a volume of the each sample of the 5-8 samples taken in step 2), wherein the 5-8 samples have the equal volume; and
   in step 7), a temperature is controlled to be 20-30° C. during a concentration under the reduced pressure, and a vacuum degree is 0.025-0.05 MPa.

2. The method according to claim 1, wherein cooling time in steps 2) and 3) is 10-30 minutes, and the first-stage Maillard reaction solutions are cooled to 10° C. or below to terminate the first-stage Maillard reaction.

3. The method according to claim 1, wherein the second-stage Maillard reaction solutions at the increased temperature in step 4) are diluted 2-50 times with distilled water.

* * * * *